(12) United States Patent
Frank

(10) Patent No.: US 7,124,758 B1
(45) Date of Patent: *Oct. 24, 2006

(54) DEVICE FOR TREATING SNORING AND OBSTRUCTIVE SLEEP APNEA

(76) Inventor: Simon Jacob Frank, 10285 SW. 23 Ct., Davie, FL (US) 33324

( * ) Notice: Subject to any disclaimer, the term of this patent is extended or adjusted under 35 U.S.C. 154(b) by 0 days.

This patent is subject to a terminal disclaimer.

(21) Appl. No.: 11/343,298

(22) Filed: Jan. 31, 2006

(51) Int. Cl.
*A61F 5/56* (2006.01)
*A47B 7/00* (2006.01)

(52) U.S. Cl. .......................................... 128/848; 5/622

(58) Field of Classification Search ................ 128/876, 128/845, 869, 846, 848, 857–862; 5/621, 5/630, 636–638, 101–103, 733, 652; 602/902, 602/17; 2/171, 171.2
See application file for complete search history.

(56) References Cited

U.S. PATENT DOCUMENTS

| | | | |
|---|---|---|---|
| 649,896 A * | 1/1900 | Baughman | ................... 128/848 |
| 904,760 A | 11/1908 | Cutting | |
| 1,339,865 A | 5/1920 | Rothenberger | |
| 1,587,558 A * | 6/1926 | Sheffield | ...................... 128/848 |
| 1,990,411 A | 2/1935 | Lowry | |
| 1,997,931 A | 4/1935 | Hoey | |
| 4,782,832 A * | 11/1988 | Trimble et al. | ........ 128/207.18 |
| 4,836,219 A | 6/1989 | Hobson et al. | |
| 5,361,416 A * | 11/1994 | Petrie et al. | .................. 2/171.2 |
| 5,893,365 A | 4/1999 | Anderson | |
| 6,016,807 A | 1/2000 | Lodge | |
| 6,058,935 A | 5/2000 | Talley | |
| 6,279,577 B1 | 8/2001 | Savaiano | |
| 7,032,597 B1 * | 4/2006 | Frank | .......................... 128/846 |

* cited by examiner

*Primary Examiner*—Henry Bennett
*Assistant Examiner*—Shumaya B. Ali
(74) *Attorney, Agent, or Firm*—Ruben Alcoba, Esq.

(57) ABSTRACT

A device that prevents obstructive sleep apnea and snoring. The device includes a headband and two belts. The headband is placed on the head of a user and the belts are attached to the front of the headband, the belts are crossed over the top of the users head and then are made to go from the back of the users neck to cross under the users chin and then to attach to the front part of the headband.

4 Claims, 3 Drawing Sheets

DEVICE FOR TREATING SNORING AND OBSTRUCTIVE SLEEP APNEA

BACKGROUND

Snoring and obstructive sleep apnea remain common and serious medical problems in spite of many medical and surgical advances in their treatment.

Snoring afflicts millions of people worldwide. Snoring is disruptive to other people in the room and the chronic fatigue that follows sleep deprivation is a serious medical problem.

The cause of snoring is turbulent air-flow setting up vibration in the palate and other soft tissues of the upper airway.

A percentage of the people who snore also suffer from obstructive sleep apnea, a condition in which a person repeatedly stops and starts breathing as many as 20 to 30 times an hour.

Obstructive sleep apnea decreases oxygen levels in the body causing daytime fatigue, cardiovascular problems and may result in death.

The causes of obstructive sleep apnea include redundant soft tissues of the airway and relaxation of the muscles at the back of the throat. Another cause pertinent to the present invention is that the tongue is pulled backward (posteriorly) into the pharynx and blocks the upper airway in a sleeping person who is in the supine position. The tongue is pulled backward by the force of gravity.

The tongue is attached to the base of the lower jaw causing the tongue and the lower jaw to move forward and backward together. This anatomical fact is the basis of the 'jaw thrust technique' used by anesthesiologists and emergency medical personnel to reestablish a compromised upper airway in unconscious people.

Moving the lower jaw forward will open the upper airway by moving the tongue forward.

The increased airflow that results from relieving the upper airway obstruction reduces airflow turbulence thereby reducing snoring and treats the obstructive sleep apnea.

Therapies used in the past to treat snoring and obstructive sleep apnea include straps, dental devices, continuous positive airway pressure (CPAP) and surgical procedures.

Straps presently being sold have proved ineffective in reducing snoring and obstructive sleep apnea. Simply closing the mouth of a sleeper who is in the supine position does not stop the force of gravity from pulling the lower jaw and the tongue backward (posteriorly) and obstructing the upper airway. The lower jaw slowly slides backward (posteriorly) unless the straps are fastened tightly enough to be uncomfortable and cut off circulation. Some straps actually pull the lower jaw backward aggravating upper airway obstruction.

Some dental devices which move the lower jaw forward, CPAP and surgery are recognized and frequently recommended modalities of treatment.

The present invention, keeps the lower jaw forwards, thus simulating the 'jaw thrust technique' and has proved effective in treating snoring and obstructive sleep apnea by relieving upper airway obstruction. The user initially advances the lower jaw forward and anteriorly and locks his jaws together with the front lower teeth touching the back of the front upper teeth. The straps maintain this position during sleep because the straps pull forwards (anteriorly) from behind the angle of the jaw.

CPAP machines and surgery are expensive method of treating people afflicted with sleep apnea and snoring. There is a need for a simple and inexpensive device to treat millions of people afflicted with snoring and obstructive sleep apnea.

An object of this invention is to relieve obstructive sleep apnea and reduce associated morbidity.

Another object of this invention is to relieve snoring and associated chronic fatigue.

A further object of this invention is to provide a device that is inexpensive and readily affordable.

Yet another object of this invention is to provide a device that is comfortable and does not in itself interrupt sleep.

Another object of this invention is to provide a device that is readily available and is easily transported.

SUMMARY

The present invention is directed to a device that prevents obstructive sleep apnea and snoring. The device satisfies the following needs: it allows a user to relieve obstructive sleep apnea and reduce associated morbidity; it allows the user to relieve snoring and associated chronic fatigue; it is a device that provides a device that is readily available and is easily transported; it provides a device that is comfortable and does not in itself interrupt sleep; and provides a device that is inexpensive and readily affordable.

The device includes a headband and two belts. The headband has front and rear sections. The rear of the headband section has two apertures defined therein. The headband section also has two tightening means. Each belt section has a first and a second end. The first end of each belt section attaches to the front of the headband. The first end of the belt sections is positioned on the headband so that the belts form an X-Junction on the apex of a user's head. The belt sections cross over one another at the apex of a patient's head and are attached to each other at the X-junction. The second end of each belt section inserts through each aperture of the rear section of the headband. The first end of each belt has a hook and loop belt fastener receiver that is positioned and is attached on the side of each belt section not attached to the headband. The second end of each belt section has a hook and loop belt fastener attachment means attached to the same side of belt section attached to the headband. The hook and loop belt fastener attachment means is positioned so that when the device is placed on the user, the second end of each belt section will pass under the chin of the user and attach to each hook and loop belt fastener receiver.

DRAWINGS

These and other features, aspects, and advantages of the present invention will become better understood with regard to the following description, appended claims, and drawings where:

WRITTEN DESCRIPTION

Figure 1:
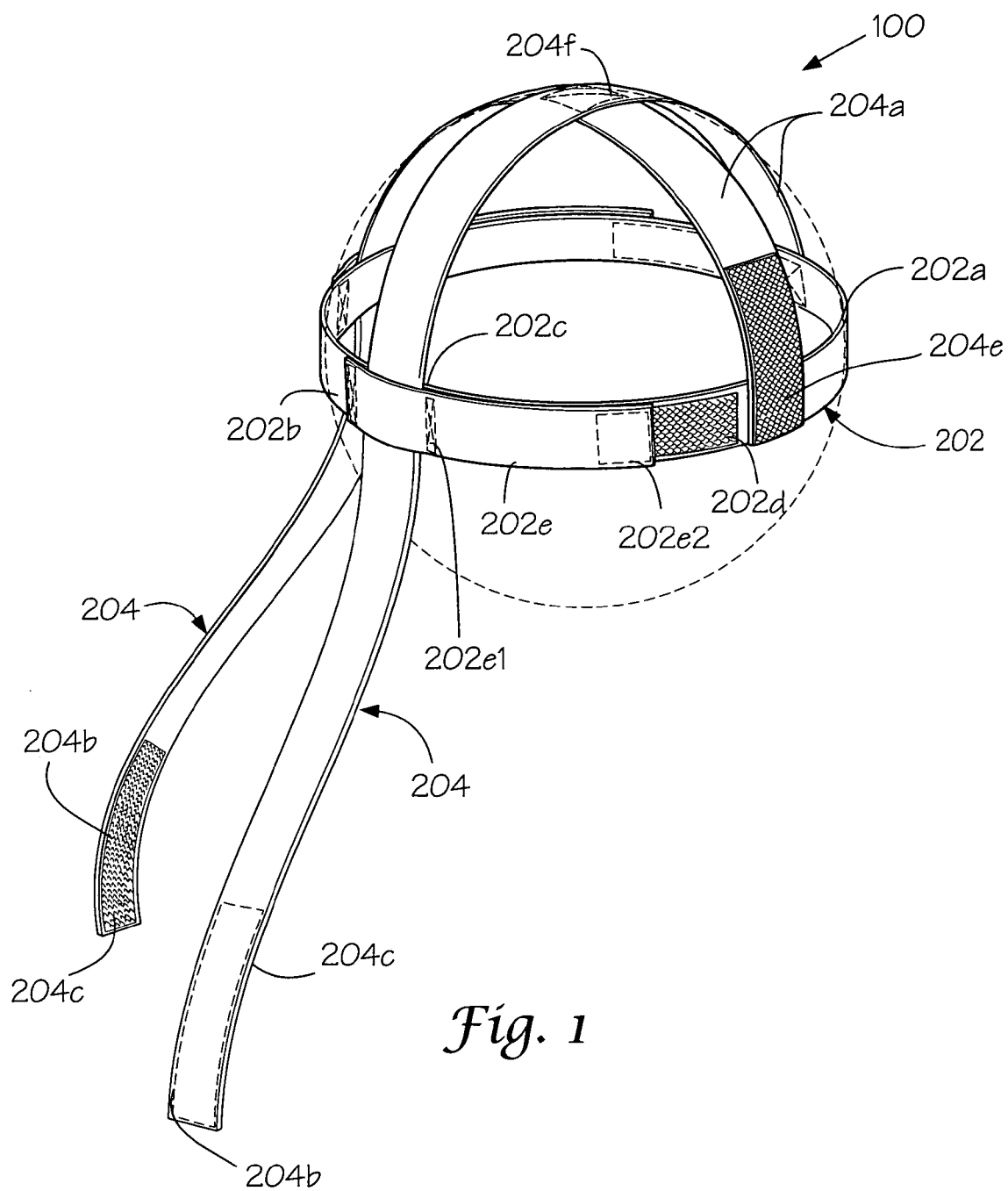
FIG. 1 shows a lateral view of a device to prevent obstructive sleep apnea and snoring.
Figure 2:
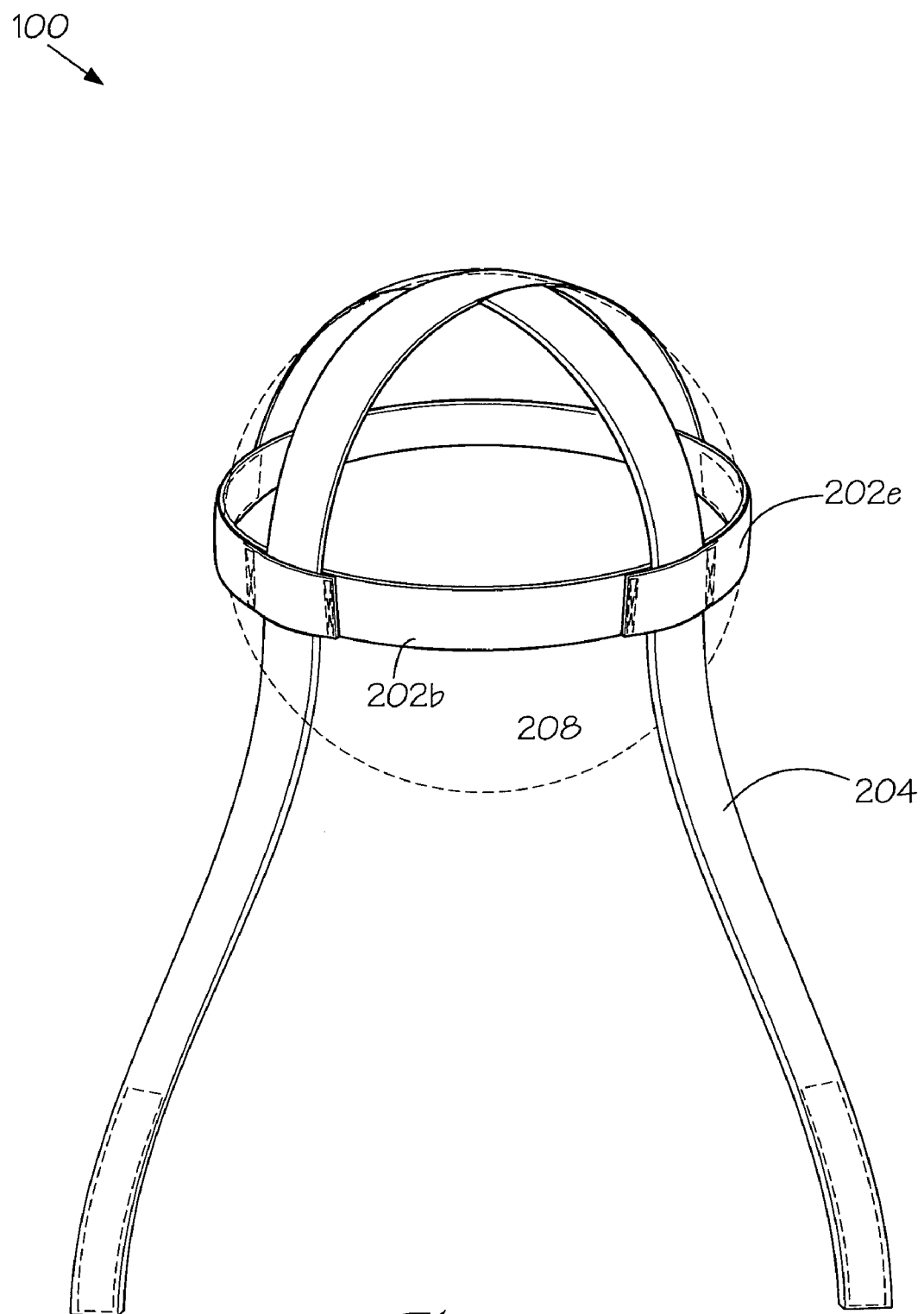
FIG. 2 illustrates a rear view of the device.

As seen in FIGS. 1–2, a device that prevents obstructive sleep apnea and snoring 100 comprises a headband 202, the headband 202 having front 202a and rear 202b sections, wherein the rear of the headband 202b has two apertures 202c defined therein, and the headband 202 has two tightening means 202e; and two belt sections 204, each belt section 204 having a first 204a and a second end 204b, the first end 204a of each belt section 204 attached to the front of the headband 202, the first end of the belt sections 204a are positioned on the headband 202 so that the belt sections 204 form an X-junction on the apex of a user's head, the belt sections are crossed over one another and attached to each other at the X-junction 204f and the second end of each belt section 204 b inserts through each aperture 202c of the rear section of the headband 202, the first end of each belt section 204a further comprising a hook and loop belt fastener receiver 204e that is positioned and is attached on the side of each belt section not attached to the headband 202, the second end of each belt section 204b has a hook and loop belt fastener attachment means 204c attached to the same side of belt section attached to the headband 202 at a position that allows the device to be placed on a user and each second end belt section 204b pass under the chin of the user so that each hook and loop attachment means 204 c attaches to each hook and loop belt fastener receiver 204e.

Figure 3:
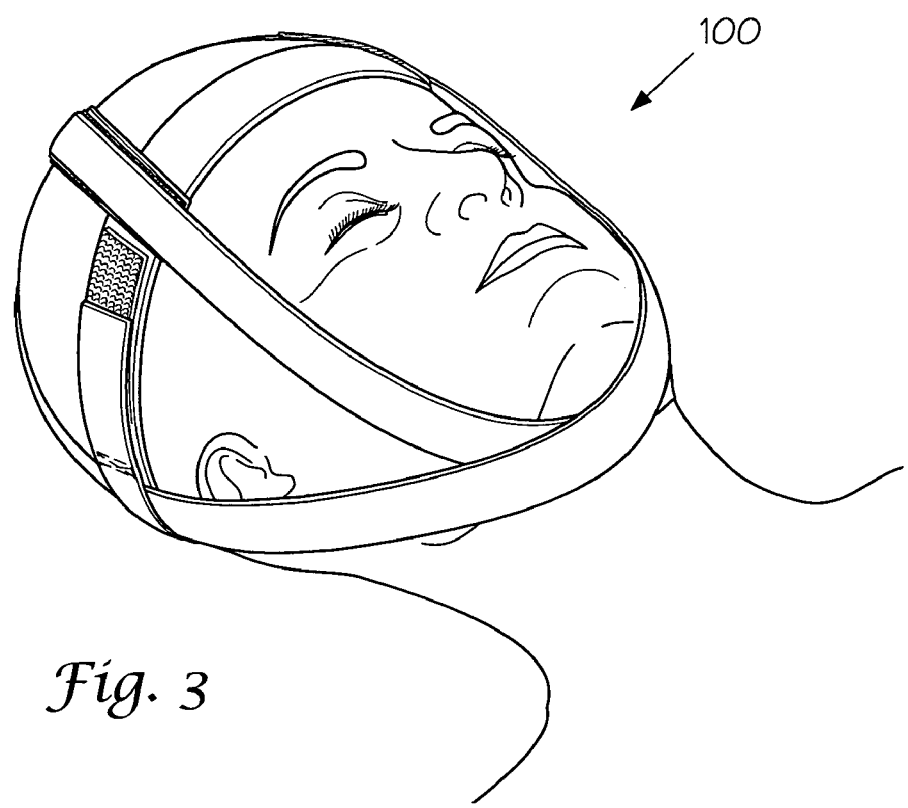
FIG. 3 shows the device on a user.
Figure 4:
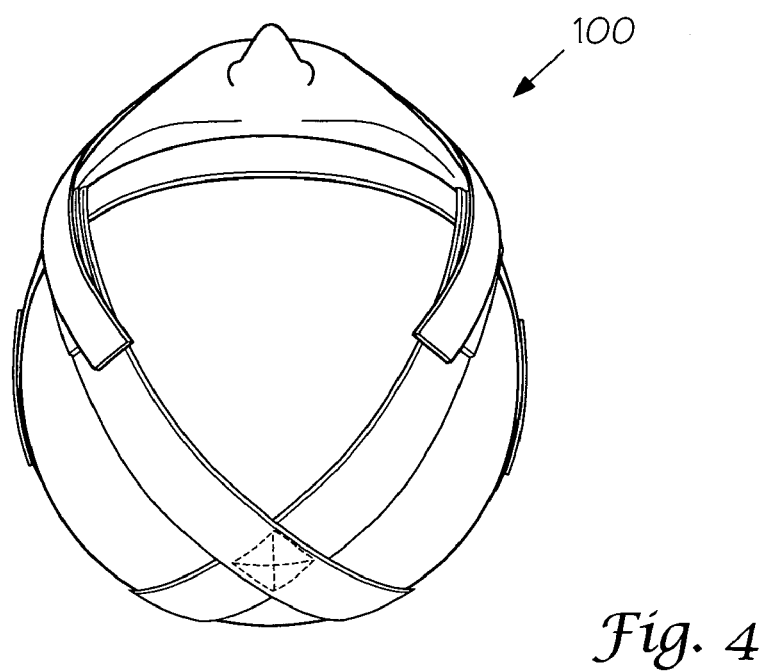
FIG. 4 shows a rear view of the device on the user.

As seen in FIGS. 1 and 3, the tightening means of the headband 202 comprises two tension strips 202e attached to the headband 202, each strip having a first 202e1 and a second end 202e2, the first end of each strip 202e1 attached to the headband 202, and the second end of each strip having a strip attachment means 202e2 attachable to a headband receiving location 202d. The strip attachment means 202e2 can be a hook and loop fastener and the headband receiving location 202d can also be a hook and loop fastener.

The device is made of any material known in the art of headbands and anti-snoring devices.

A method of using the invention in FIGS. 1–4, which comprises the steps of first, threading the belts 204 through the headband's apertures 202c. Next, placing the headband 202 around the head of a user so that the adjustable ends of the belts 204b of the device 100 flow from the back of the head and down the back of the neck of the user. Then, tightening the tightening means 202e of the headband 202. Next, having the user advance user's lower jaw forward at least to a point where the user's lower front teeth are in contact with the user's upper front teeth. Then, pulling the adjustable ends of the belts 204b. Next, crossing the belts 204 under the lower jaw of the user so that each belt 204 is passed from behind the angle of the jaw and placed as far forwards as possible under the apex of the chin of the user. Lastly, attaching the belt hook and loop belt fastener attachment means 204c to the hook and loop belt fastener receiver 204e so that sufficient tension is maintained to keep the jaws locked together and the front teeth of the lower jaw in contact with the front teeth of the upper jaw.

An advantage of this invention is that it relieves obstructive sleep apnea and reduces associated morbidity.

Another advantage of this invention is that it relieves snoring and associated chronic fatigue.

A further advantage of this invention is that it provides a device that is inexpensive and readily affordable.

Yet another advantage of this invention is that it provides a device that is comfortable and does not in itself interrupt sleep.

Another advantage of this invention is that it provides a device that is readily available and is easily transported.

Another advantage of this invention is that it provides an inexpensive way of treating sleep apnea.

Although the present invention has been described in considerable detail with reference to certain preferred versions thereof, other versions are possible. Therefore the spirit and the scope of the claims should not be limited to the description of the preferred versions contained herein.

What is claimed is:

1. A device that prevents obstructive sleep apnea and snoring, comprising:

a headband, the headband having front and rear sections, wherein the rear of the headband has two apertures defined therein, and the headband has two tightening means; and two belt sections, each belt section having a first and a second end, the first end of each belt section attached to the front of the headband, the first end of the belt sections are positioned on the headband so that the belt sections form an X-junction on the apex of a user's head, the belt sections are crossed over one another and attached to each other at the X-junction and the second end of each belt section inserts through each aperture of the rear section of the headband, the first end of each belt section further comprising a hook and loop belt fastener receiver that is positioned and is attached on the side of each belt section not attached to the headband, the second end of each belt section has a hook and loop belt fastener attachment means attached to the same side of belt section attached to the headband at a position that allows the device to be placed on a user and each second end belt section pass under the chin of the user so that each hook and loop attachment means attaches to each hook and loop belt fastener receiver.

2. The device of claim 1, wherein the tightening means comprises two tension strips attached to the headband, each strip having a first and a second end, the first end of each strip attached to the headband, and the second end of each strip having a strip attachment means attachable to headband receiving location.

3. The device of claim 2, wherein the strip attachment means and the headband receiving location are hook and loop fasteners.

4. A method of using the device of claim 1, comprising the steps of:

first, threading the belts through the headband's apertures;

next, placing the headband around the head of a user so that the adjustable ends of the belts of the device flow from the back of the head and down the back of the neck of the user;

then, tightening the tightening means of the headband;

next, having the user advance user's lower jaw forward at least to a point where the user's lower front teeth are in contact with the user's upper front teeth;

then, pulling the adjustable ends of the belts;

next, crossing the belts under the lower jaw of the user so that each belt is passed from behind the angle of the jaw and placed as far forwards as possible under the apex of the chin of the user; and lastly, attaching the belt hook and loop belt fastener attachment means to the hook and loop belt fastener receiver so that sufficient tension is maintained to keep the jaws locked together and the front teeth of the lower jaw in contact with the front teeth of the upper jaw.

* * * * *